United States Patent
Luoh et al.

(10) Patent No.: US 8,085,390 B2
(45) Date of Patent: Dec. 27, 2011

(54) MULTIVARIATE MONITORING METHOD FOR PLASMA PROCESS MACHINE

(75) Inventors: Tuung Luoh, Hsinchu (TW); Shing-Ann Luo, Hsinchu (TW); Chin-Ta Su, Hsinchu (TW); Ta-Hung Yang, Hsinchu (TW); Kuang-Chao Chen, Hsinchu (TW)

(73) Assignee: MACRONIX International Co., Ltd., Hsinchu (TW)

( * ) Notice: Subject to any disclaimer, the term of this patent is extended or adjusted under 35 U.S.C. 154(b) by 299 days.

(21) Appl. No.: 11/737,541

(22) Filed: Apr. 19, 2007

(65) Prior Publication Data
US 2008/0123082 A1    May 29, 2008

(30) Foreign Application Priority Data
Nov. 29, 2006   (TW) ................ 95144168 A

(51) Int. Cl.
*G01N 21/00*   (2006.01)
(52) U.S. Cl. ........................................ 356/72
(58) Field of Classification Search .................. 356/72, 356/303, 316, 336, 337
See application file for complete search history.

(56) References Cited

U.S. PATENT DOCUMENTS

| 6,673,200 B1 | 1/2004 | Gu et al. |
| 6,837,965 B2 | 1/2005 | Gustafson et al. |
| 6,919,279 B1 | 7/2005 | Rulkens et al. ............ 438/706 |
| 6,972,840 B1 * | 12/2005 | Gu et al. .................... 356/337 |
| 2004/0026035 A1 | 2/2004 | Mitrovic ................ 156/345.24 |
| 2005/0055175 A1 * | 3/2005 | Jahns et al. ................ 702/182 |
| 2005/0078310 A1 * | 4/2005 | Rueger et al. ............. 356/316 |
| 2005/0082482 A1 * | 4/2005 | Ludviksson ............... 250/342 |
| 2006/0102847 A1 | 5/2006 | Shelley et al. ............. 250/372 |

FOREIGN PATENT DOCUMENTS

| TW | 455973 | 9/2001 |
| WO | WO 02/48683 | 6/2002 |

OTHER PUBLICATIONS

Chinese Examination Report of Taiwan Application No. 095144168, dated Aug. 13, 2009.
Chinese Examination Report of Taiwan Application No. 095144168, dated Apr. 14, 2010.

* cited by examiner

*Primary Examiner* — Tarifur Chowdhury
*Assistant Examiner* — Abdullahi Nur
(74) *Attorney, Agent, or Firm* — J.C. Patents

(57) ABSTRACT

An advance process control (APC) system for a plasma process machine is provided, which includes at least an optical emission spectroscopy (OES) system and an APC analysis apparatus. The OES system is used for monitoring a testing object in the plasma process machine. The APC analysis apparatus is used for analyzing the data received from the OES system.

9 Claims, 2 Drawing Sheets

MULTIVARIATE MONITORING METHOD FOR PLASMA PROCESS MACHINE

CROSS-REFERENCE TO RELATED APPLICATION

This application claims the priority benefit of Taiwan application serial no. 95144168, filed Nov. 29, 2006. All disclosure of the Taiwan application is incorporated herein by reference.

BACKGROUND OF THE INVENTION

1. Field of the Invention

The present invention relates to a plasma process application system. More particularly, the present invention relates to an advance process control (APC) system and a multivariate analysis monitoring method for a plasma process machine.

2. Description of Related Art

Plasma process is one of the most important processes in semiconductor process, which may include processes such as deposition, etching, and cleaning. In particular, plasma-enhanced deposition process, such as plasma-enhanced chemical vapor deposition (PECVD) or high density plasma CVD, has been broadly applied to film depositions in semiconductor devices. Usually different material layers are obtained by changing various parameters of a plasma process machine within a plasma deposition chamber.

However, when abnormity occurs in a plasma process due to the instability of the plasma process machine, the abnormal semiconductor device cannot be detected with existing testing method until the entire semiconductor device has been completed. Therefore, the manufacturing cost is very high and the process time is also wasted.

Accordingly, a method for stabilizing the plasma process machine and an apparatus thereof is very important.

SUMMARY OF THE INVENTION

Accordingly, the present invention is directed to an advanced process control (APC) system for a plasma process machine.

The present invention is also directed to a multivariate analysis monitoring method detecting abnormity in a plasma process machine on a real time basis. The present invention provides an APC system for a plasma process machine. The APC system includes at least an optical emission spectroscopy (OES) system and an APC analysis apparatus. The OES sensors are utilized CCD array detection for detect plasma spectrum during process, it is possible to rapidly collect (2-10 Hz) full spectral data (200-900 nm in wavelength), consisting of over 1000 discrete wavelength channels from a plasma process.

The OES system is suitable for a multivariate monitor to a testing object in the plasma process machine, and the APC analysis apparatus is used for analyzing the data received from the OES system.

According to an embodiment of the present invention, the APC analysis apparatus includes at least a spectrum database for storing spectroscopy data from the OES system.

According to an embodiment of the present invention, the APC analysis apparatus includes a fault detection and classification (FDC) system for processing the data stored in the spectrum database.

According to an embodiment of the present invention, the APC analysis apparatus includes a multivariate analysis system for analyzing the data stored in the spectrum database.

According to an embodiment of the present invention, the APC analysis apparatus includes an equipment health monitoring (EHM) system.

According to an embodiment of the present invention, the APC analysis apparatus includes a predictive clean system.

According to an embodiment of the present invention, the APC analysis apparatus calculates an integral of a spectrum intensity function within a specific wavelength range obtained from the OES system and determines whether or not the spectrum is abnormal according to the integral.

According to an embodiment of the present invention, the APC analysis apparatus obtains the spectra of films formed in the same plasma process machine with different plasma processes and the same material from the OES system, and the APC analysis apparatus compares the spectrum intensities of the films within a short wavelength range to determine a spectrum having lower spectrum intensity as a selected spectrum.

According to an embodiment of the present invention, the APC analysis apparatus compares the spectra of a lot of chips obtained from the OES system to monitor the stability and repeatability of the lot of chips.

According to an embodiment of the present invention, the APC analysis apparatus compares the spectrum of the testing object obtained from the OES system and a standard spectrum to determine whether or not the testing object conforms to a standard.

According to an embodiment of the present invention, the APC analysis apparatus compares the spectra of a plurality of chips obtained from the OES system to find out an abnormal spectrum, wherein the chip having the abnormal spectrum is damaged during a plasma process due to abnormal chip temperature.

According to an embodiment of the present invention, the APC analysis apparatus determines an open chamber clean time point of the plasma process machine according to the reduction of spectrum intensity of the internal wall of the plasma process machine obtained from the OES system along time.

According to an embodiment of the present invention, the OES system is a charge-coupled device (CCD) array system.

According to an embodiment of the present invention, the OES system obtains a full spectrum of a testing object in the plasma process machine.

According to an embodiment of the present invention, the plasma process machine includes a high density plasma chemical vapor deposition (HDPCVD) machine.

According to an embodiment of the present invention, the plasma process machine includes a plasma etching machine.

According to an embodiment of the present invention, the testing object includes a deposited layer.

According to an embodiment of the present invention, the testing object includes an etched layer.

According to an embodiment of the present invention, the testing object includes the internal wall of the plasma process machine.

The present invention provides a multivariate analysis monitoring method for a plasma process machine. The method includes obtaining a spectrum of a testing object from a plasma process machine by using an OES system and analyzing the spectrum by using an APC analysis apparatus.

According to another embodiment of the present invention, the step of analyzing the spectrum by using the APC analysis apparatus is to calculate an integral of the spectrum intensity function within a predetermined wavelength range and determine whether or not the spectrum is abnormal according to the integral. Here, the testing object may be a deposited layer.

Besides, if a restricted range has been preset in the plasma process machine and the spectrum of the deposited is determined to be abnormal, the spectrum of the deposited layer is considered exceeding the restricted range and a warning signal is issued, or parameters of the plasma process machine are adjusted after analyzing the spectrum.

According to another embodiment of the present invention, the testing object includes a plurality of films formed in the same plasma process machine through different plasma processes using the same material with slightly different element proportions. Accordingly, the step of analyzing the spectrum by using the APC analysis apparatus includes analyzing the spectra of the films by comparing the spectrum intensities thereof within a short wavelength range and determining a selected spectrum according to the comparison result, wherein the selected spectrum is a spectrum having lower spectrum intensity among the spectra of the films. A plasma process corresponding to the selected spectrum is used for fabricating the films. Besides, the selected spectrum may be the spectrum having the lowest spectrum intensity among the spectra of the films.

According to another embodiment of the present invention, the testing object may be a lot of chips. Thus, the step of analyzing the spectrum by using the APC analysis apparatus includes comparing the spectra of the lot of chips to monitor the stability and reproducibility of the lot of chips. Moreover, the step of comparing the spectra of the lot of chips includes selecting a wavelength range and comparing the spectrum intensity of each chip of the lot of chips within the wavelength range. The lot of chips includes chips obtained by executing the same program.

According to another embodiment of the present invention, the testing object may include a standard film and a tested film. Thus, the step of analyzing the spectrum by using the APC analysis apparatus includes comparing the spectrum of the tested film and the spectrum of the standard film to determine whether or not the tested film conforms to a standard. For example, if the standard film has a reflective index, a refractive index (RI, also referred to as value n), and extinction coefficient (also referred to as value k) within a restricted range and the tested film is determined as not conforming to the standard, it can be deduced that at least one of the reflective index, value n, and value K of the tested film has exceeded the restricted range.

According to another embodiment of the present invention, the testing object may be a plurality of chips, and a tested film is formed on each chip, wherein the tested film is manufactured through the same plasma process in the same plasma process machine. In this case, the step of analyzing the spectrum by using the APC analysis apparatus includes comparing the spectra of various tested films to determine an abnormal spectrum, wherein the tested film having the abnormal spectrum is damaged during the plasma process due to abnormal chip temperature.

According to another embodiment of the present invention, the testing object includes the internal wall of the plasma process machine. Thus, the step of analyzing the spectrum by using the APC analysis apparatus includes determining an open chamber clean time point of the plasma process machine according to the reduction in the spectrum intensity obtained at time intervals.

According to another embodiment of the present invention, the testing object includes an etched layer. Thus, the step of analyzing the spectrum by using the APC analysis apparatus includes determining an etching endpoint according to the spectrum intensity variation of the testing object.

According to another embodiment of the present invention, the OES system is a CCD array system.

According to another embodiment of the present invention, the plasma process machine includes a high density plasma machine or a plasma etching machine.

According to the present invention, the spectrum of a tested film in a plasma process machine is obtained on real time basis so that the stability of the process can be improved by monitoring and controlling the spectrum and the spectrum can be used as a feature and index for monitoring process parameters and reproducibility. Moreover, whether or not a characteristic of a deposited film being changed can be detected measuring the spectrum intensity.

In order to make the aforementioned and other objects, features and advantages of the present invention comprehensible, preferred embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
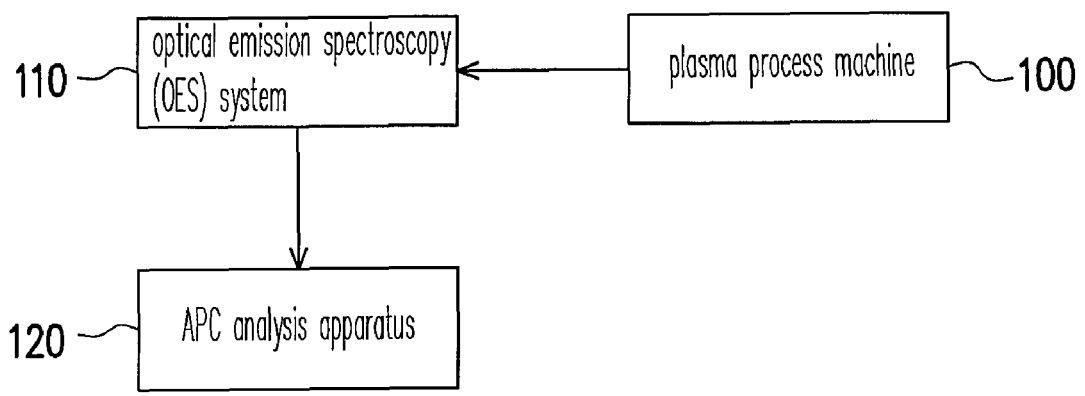
FIG. 1 is a schematic block diagram of an advance process control (APC) system for a plasma process machine according to a first embodiment of the present invention.

FIG. 1 is a schematic block diagram of an advance process control (APC) system for a plasma process machine according to a first embodiment of the present invention.

Referring to FIG. 1, in the present embodiment, the APC system includes an optical emission spectroscopy (OES) system 110 and an APC analysis apparatus 120.

The OES technique is a non-invasive measurement method which can focus emission signals of excited atoms, ions, molecules in plasma to an optical fiber head by using a collimator and then bring the light into a spectrophotometer along the optical fiber for analyzing the spectral lines and intensity of the plasma emission spectrum. In the present embodiment, the OES system 110 is for multivariate monitor to a testing object in a plasma process machine 100 which may include a high density plasma (HDP) machine or a plasma etching machine. In particular, the OES system 110 can directly test the testing object in the plasma process machine 100 right after a plasma process is completed. Thus, the required data, such as the full spectrum of the testing object, can be instantly obtained. The OES system 110 may be a charge-coupled device (CCD) array system. the CCD array system can store information therein. For example, a grating with multiple slits may be used to control the projection of the spectrum of output light beams from the plasma process machine 100 onto the multiple elements of a photo-diode sensor array, such as an array in the CCD array system. That is, the spectrometer splits the optical emissions from the viewport into its full spectrum and the grating enables the different spectral elements from the spectrum to be projected onto different parts of the CCD array.

In FIG. 1, the APC analysis apparatus 120 analyzes the data received from the OES system 110. And, the APC analysis apparatus 120 provides system for data acquisition, data storage, data analysis and user interface in general. For example, foresaid data access from tools SECS (8" FA port) and HSMS (12" FA port). Furthermore, the APC analysis apparatus 120 is utilized to multi-variable mathematical analysis for process modeling monitoring and FDC (fault detection and classification). Besides, the APC analysis apparatus 120 has performances of Auto collecting tools' alarms, and clarify alarm Type, alarm Count, alarm Run and Total Run. Additionally, the APC analysis apparatus 120 can do statistics analysis of alarms to enhance capability of tools management or real-time monitoring for tools status, chamber status, and process parameters. Moreover, the APC analysis apparatus 120 belongs to an auto-notifies tool, accesses check-list for quick problem resolution. For example, in the present embodiment according to the present invention, the APC analysis apparatus 120 may include one or multiple sub-systems such as a spectrum database storing spectrum data from the OES system 110, a FDC system for processing data stored in the spectrum database, a multivariate analysis system for analyzing the data stored in the spectrum database, an equipment health monitoring (EHM) system, and a predictive clean system.

Figure 2:
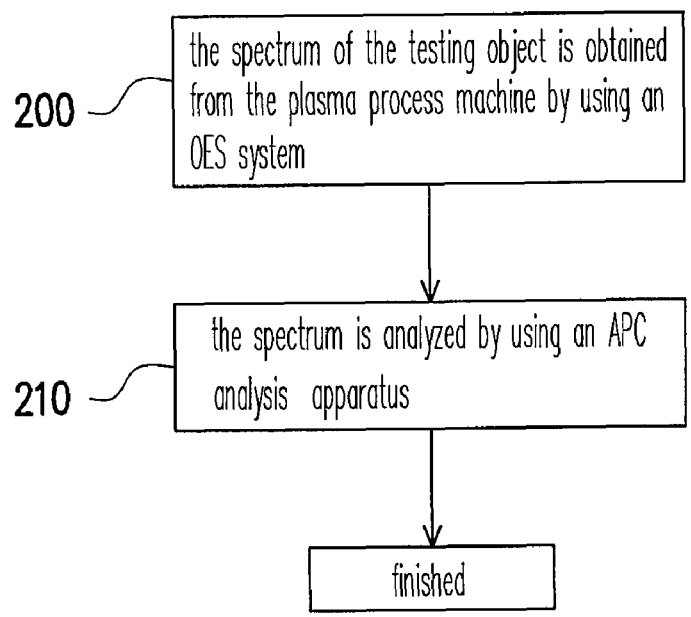
FIG. 2 is a flowchart illustrating a multivariate analysis monitoring method for a plasma process machine according to a second embodiment of the present invention.

FIG. 2 is a flowchart illustrating a multivariate analysis monitoring method for a plasma process machine according to a second embodiment of the present invention.

Referring to FIG. 2, in step 200, the spectrum of the testing object is obtained from the plasma process machine by using an OES system. In the second embodiment, the OES system may be a CCD array. Next, in step 210, the spectrum is analyzed by using an APC analysis apparatus.

Several applications of the APC system in the present invention will be described below, and they are not intended for limiting the scope of the present invention.

Figure 3:
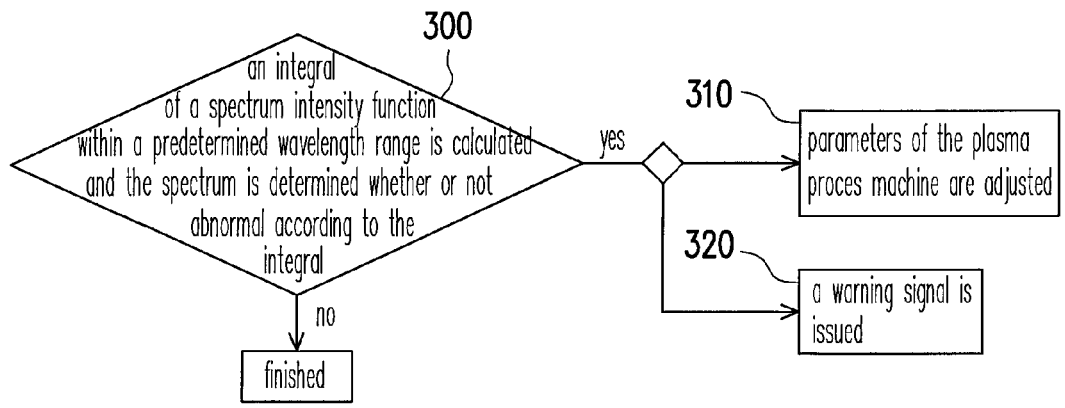
FIG. 3 is a flowchart illustrating a first application of step 210 in FIG. 2.

FIG. 3 is a flowchart illustrating a first application of step 210 in FIG. 2.

Referring to FIG. 3, after obtaining the spectrum of the testing object (for example, a deposited layer) from the plasma process machine by using the OES system, step 300 is executed to calculate an integral of a spectrum intensity function within a predetermined wavelength range and determine whether or not the spectrum is abnormal according to the integral. The monitoring step is completed if the spectrum is determined to be normal.

The spectrum of the foregoing deposited layer is considered exceeding a restriction range preset by the plasma process machine if the spectrum is determined to be abnormal. Next, step 310 may be executed to adjust parameters of the plasma process machine or step 320 may be executed to issue a warning signal.

Figure 4:
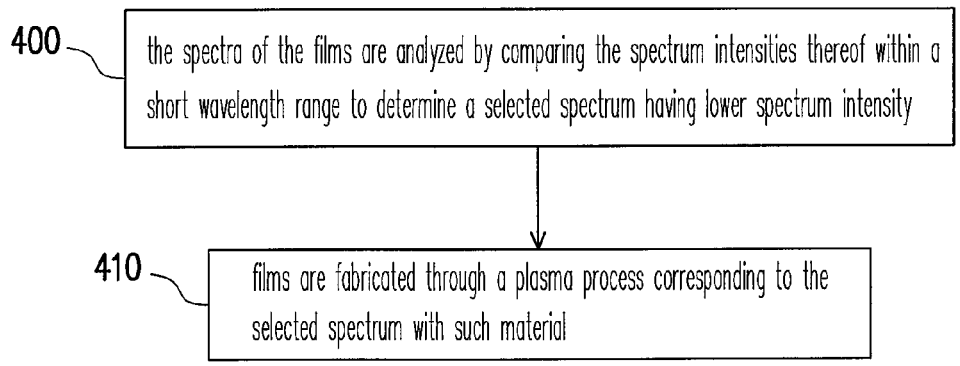
FIG. 4 is a flowchart illustrating a second application of step 210 in FIG. 3.

FIG. 4 is a flowchart illustrating a second application of step 210 in FIG. 3.

Referring to FIG. 4, the testing object includes various films formed in the same plasma process machine through different plasma processes with the same material having slightly different element proportions. For example, such films may include a variety of material layers in a semiconductor device, such as an oxide layer or a nitride layer used as a gate dielectric layer. The analysis process in step 210 may include following steps. First, in step 400, the spectra of the films are analyzed by comparing the spectrum intensities thereof within a short wavelength range (such as the wavelength range of UV light) to determine a selected spectrum having lower spectrum intensity, preferably, the spectrum having the lowest spectrum intensity, as a selected spectrum. For example, generally the performance of a gate oxide layer in a semiconductor device may be affected when the electronic energy is higher than 3.2 eV due to plasma damage, and according to a calculation result, spectrum intensity with a wavelength (denoted as $\lambda$) lower than 400 nm may affect the performance of the gate oxide layer greatly. Thus, the selected spectrum can be determined based on a wavelength of 400 nm.

Next, in step 410, films are fabricated through a plasma process corresponding to the selected spectrum with such material. Accordingly, films are fabricated through a plasma process which would not cause high spectrum intensity so that abnormal plasma process can be monitored and prevented from damaging devices. Furthermore, the semiconductor devices can be prevented from being damaged by the plasma.

In the present embodiment, some parameters of the plasma deposition process may be selected as references according to existing standard and the parameters which give the lowest plasma damage may be selected as the process parameters. Thus, the multivariate analysis monitoring method in the present invention may be further used as a method for determining plasma process parameters, so as to prevent plasma damage, with existing parameter selection and determination structure.

According to a third application of step 210 in the second embodiment, when the testing object is a lot of chips, the step of analyzing the spectrum of the testing object includes comparing the spectra of the lot of chips, so as to monitor the stability and reproducibility of the lot of chips. For example, the step of comparing the spectra of the lot of chips may include selecting a wavelength range first and comparing the spectrum intensity of each chip in the lot of chips within the wavelength range. If there is an abnormal spectrum in the spectra of the lot of chips, the specific abnormal spectrum may be analyzed individually to determine and resolve the excursion issue within a short time. Besides, the "lot" of chips here refers to chips obtained by executing the same program.

According to a fourth application of step 210 in the second embodiment, when the testing object includes a standard film and a tested film, the spectrum of the tested film and the spectrum of the standard film are compared to determine whether or not the tested film conforms to a standard. If the standard film has a reflective index, a value n (refractive index, RI), and a value k (extinction coefficient) within a restricted range or any other value which may be used as a standard. Such standard values may be measured using well known techniques known to those having ordinary skill in the art. Accordingly, it can be deduced that at least one of the reflective index, the value n, and the value k of the tested film exceeding the restricted ranged is determined to not conform to the standard.

According to a fifth application of step 210 in the second embodiment, when the testing object is a plurality of chips and a tested film is formed in the same plasma process machine and through the same plasma process on each of the chips, the spectra of these tested films are compared to determine an abnormal spectrum, and wherein the tested film having the abnormal spectrum is damaged during the plasma process due to abnormal chip temperature.

According to a sixth application of step 210 in the second embodiment, when the testing object is the internal wall of the plasma process machine, the spectra thereof obtained at different time intervals by the APC analysis apparatus are analyzed, and an open chamber clean time point of the plasma process machine is determined according to the reductions in the spectrum intensities of the spectra. This is because the plasma process machine may have uncontrollable abnormal situations along time and which may weaken the original self-clean capability of the plasma process machine. For example, $NF_3$ is generally used for reacting with residual $SiO_2$ to produce $N_2$, $O_2$, and $SiF_4$. Accordingly, the content of element F in the internal wall of the plasma process machine can be obtained by the OES system, and the self-clean capability of the plasma process machine is weakened when the content of element F reduces so that the entire machine has to be opened for a thorough cleaning.

According to a seventh application of step 210 in the second embodiment, when the testing object is an etched layer, an etching endpoint may be determined according to the spectrum intensity variation of the testing object.

In summary, the system and method of the present invention have at least the following advantages.

1. A spectrum of a testing object from a plasma process machine is obtained by using an OES system and analyzed by using an APC analysis apparatus, so the spectrum data can be obtained and analyzed on real time basis for controlling the stability of a plasma process.
2. A multivariate monitor is performed to the plasma process machine so that abnormal plasma process can be monitored and prevented from damaging semiconductor devices.
3. The present invention can be applied to a plasma process for mass production of chips, and the plasma can be monitored by monitoring the spectrum characteristic of the plasma process so that the excursion issue may be determined and resolved in very short time. Thus, the problem of WAT can be effectively prevented.
4. Parameters (for example, reflective index, value n, and value k, etc) of a plasma deposited layer can be monitored and controlled through spectrum variation thereof.
5. The present invention may also be used for resolving the problem of damaged semiconductor device due to abnormal chip temperature during a plasma process.
6. The present invention may also be applied to determine an open chamber clean time point, so as to predict when to perform open chamber clean.
7. The OES system in the APC system can be used for detecting an etching endpoint.
8. Since the APC system can be used for various detection and application, various problems during a plasma process can be determined and resolved so that the time and the manufacturing cost can be effectively reduced.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of fabricating a film using a plasma process machine, comprising:
    obtaining a spectrum of a plurality of films formed in the same plasma process machine by using an OES system, wherein the plurality of films comprise the same material with different element proportions;
    analyzing the spectrum of each film by comparing spectrum intensities within a wavelength range;
    determining a selected spectrum, wherein the selected spectrum is a spectrum having a lowest spectrum intensity among the spectra of the films; and
    fabricating a film of the material using a plasma process corresponding to the selected spectrum.

2. The method as claimed in claim 1, wherein the film comprises an oxide layer or a nitride layer.

3. The method as claimed in claim 1, wherein the wavelength range is a wavelength range of UV light.

4. A method of determining if at least one of a reflective index, a refractive index, and an extinction coefficient of a tested film exceeds a restricted ranged, comprising:
    obtaining a spectrum of a standard film from a plasma process machine by using an OES system, wherein the standard film has a standard reflective index, a standard refractive index having a value n, and a standard extinction coefficient having a value k within the restricted range;
    obtaining a spectrum of the tested film from the plasma process machine by using the OES system, wherein the tested film has the reflective index, the refractive index having a value n, and the extinction coefficient having a value k; and
    using an APC analysis apparatus for comparing the spectrum of the tested film and the spectrum of the standard film to determine whether or not that at least one of the reflective index, the value n, and the value k of the tested film exceeds the restricted range.

5. The method as claimed in claim 4, wherein the OES system is a CCD array system.

6. The method as claimed in claim 4, wherein the plasma process machine comprises a high density plasma machine or a plasma etching machine.

7. A method for determining an open chamber clean time point of a plasma process machine, comprising:
    obtaining a plurality of spectra of an internal wall of the plasma process machine at different time intervals by using an OES system;
    measuring the plurality of spectra of the internal wall of the plasma process machine to evaluate a spectrum intensity reductions; and
    determining an open chamber clean time point of the plasma process machine according to the spectrum intensity reductions obtained at intervals by using an APC analysis apparatus.

8. The method as claimed in claim 7, wherein the OES system is a CCD array system.

9. The method as claimed in claim 7, wherein the plasma process machine comprises a high density plasma machine or a plasma etching machine.

* * * * *